US005681279A

United States Patent [19]

Roper et al.

[11] Patent Number: 5,681,279

[45] Date of Patent: Oct. 28, 1997

[54] PILL DISPENSING SYRINGE

[76] Inventors: David H. Roper; Cathy M. Roper, both of 3950 N. 183rd St. West, Colwich, Kans. 67030

[21] Appl. No.: 743,504

[22] Filed: Nov. 4, 1996

[51] Int. Cl.$^6$ .......... A61M 5/18

[52] U.S. Cl. .......... 604/57; 604/60; 606/236

[58] Field of Search .......... 604/56–64, 77, 604/79, 78; 606/234, 235, 236

[56] References Cited

U.S. PATENT DOCUMENTS

| | | | |
|---|---|---|---|
| 697,209 | 4/1902 | Koppenhagen | 604/78 X |
| 1,262,732 | 4/1918 | Andrews | 604/62 |
| 1,936,437 | 11/1933 | Peters | 604/61 X |
| 5,578,004 | 11/1996 | Liang | 606/236 X |

*Primary Examiner*—John D. Yasko
*Attorney, Agent, or Firm*—Kenneth Jack

[57] ABSTRACT

A pill dispensing syringe comprising a cylindrical outer housing, a water injection cylinder slidably mounted within the interior bore of the outer housing, a piston slidably mounted within the interior bore of the water injection cylinder, a piston rod fixedly attached to the piston and extending therefrom through the interior bores of the water injection cylinder and the outer housing, a cylindrical pill dispensing sleeve fixedly attached to the opposing end of the outer housing, the opposing end of the pill dispensing sleeve being adapted for holding a pill, and a cylindrical water injection tube slidably mounted within the interior bore of the pill dispensing sleeve, and end of the water injection tube being fixedly attached to the water injection cylinder.

14 Claims, 4 Drawing Sheets

PILL DISPENSING SYRINGE

BACKGROUND OF THE INVENTION

Oral administration of medicinal tablets and pills to small animals such as cats and dogs typically is a difficult task. A known method is to imbed a pill to be administered into a piece of meat or other food item, and to feed the pill imbedded food to the animal. A problem with this method is that the pill may become dislodged from the food prior to being swallowed. Also, the animal may learn that the type of food used contains a pill and begin to reject the food.

Another known, but problematic, method of administering a pill to a small animal is to manually insert the pill into the animal's mouth and then stroke the exterior surface of the animal's throat to induce a swallowing response. This method exposes the person administering the pill to the risk of having fingers bitten. Also, stroking the throat of the animal is an unreliable method of inducing a swallowing response.

Apparatuses known as a "pill gun" or "balling gun" represent another means of administering pills to small animals. Examples of such apparatus are described in U.S. Pat. No. 4,060,083 issued Nov. 29, 1977, to Hanson; U.S. Pat. No. 3,934,584 issued Jan. 27, 1976, to Corio; U.S. Pat. No. 3,780,735 issued Dec. 25, 1973, to Crouter, et al.; U.S. Pat. No. 3,238,941 issued Mar. 8, 1966, to Klein, et al.; U.S. Pat. No. 2,601,852 issued Jul. 1, 1952, to Wendt; U.S. Pat. No. 2,593,757 issued Apr. 22, 1952, to Hofacker; and U.S. Pat. No. 2,587,364 issued Feb. 26, 1952, to Mitchell. All of the pill gun or balling guns disclosed by the above patents serve the function of inserting a pill into an animal's mouth while protecting the hands and fingers of the person administering the pill. However, none of said patents disclose any feature or apparatus which functions to induce a swallowing response in the animal. None of the above referenced patents teach the useful, unique and novel attributes of the present invention.

Deficiencies in known methods and art of administering pills to animals creates a need for an apparatus which protectively inserts a pill into an animal's mouth and induces a swallowing response.

The present invention provides for protection of the pill administrator's fingers and hands and induces a swallowing response by providing apparatus allowing a single thrust of the thumb of a hand holding the apparatus to, in sequence, inject a pill into the animal's mouth, and inject a small amount of water into the animal's mouth inducing a swallowing reflex.

BRIEF SUMMARY OF THE INVENTION

This invention relates to a water assisted pill gun or pill dispensing syringe which is particularly adapted for administering medicinal pills, capsules, and tablets to small animals such as cats and dogs. The pill dispensing syringe is constructed so that with a single motion of the thumb of a hand holding the apparatus a pill held by the apparatus is injected into the animal's mouth, immediately followed by the injection of a small amount of water. The water induces a swallowing response, causing the pill to be swallowed.

The above objects are accomplished by means of slidably encasing a water injecting syringe within an outer housing, an end of the outer housing being adapted for holding and dispensing a pill. Through the application of compression springs installed within the casing above and below the water injection cylinder of the syringe, the tip of the injection tube of the syringe may be caused to eject a pill into the animal's mouth prior to the commencement of injection of water into the animal's mouth.

It is an object of the present invention to provide an apparatus for oral administration of pills, capsules, and tablets to small animals while protecting the hands and fingers of the person administering the pill, capsule or tablet.

It is a further object of the present invention to provide an apparatus which, in close sequence, will inject a pill into an animal's mouth and inject a small amount of water into the animal's mouth, inducing a swallowing response.

It is a further object of the present invention to provide an apparatus for water assisted oral administration of pills and tablets to animals, the apparatus having a disposable pill retaining and inserting means allowing for sanitary use of the apparatus with several animals in sequence.

It is a further object of the present invention to provide an apparatus for administration of pills to animals which is easily assembled and disassembled for purposes of sterilization.

These and other objects of the present invention will become apparent to those skilled in the art as the description thereof proceeds.

DESCRIPTION OF THE PREFERRED EMBODIMENT

Figure 1:
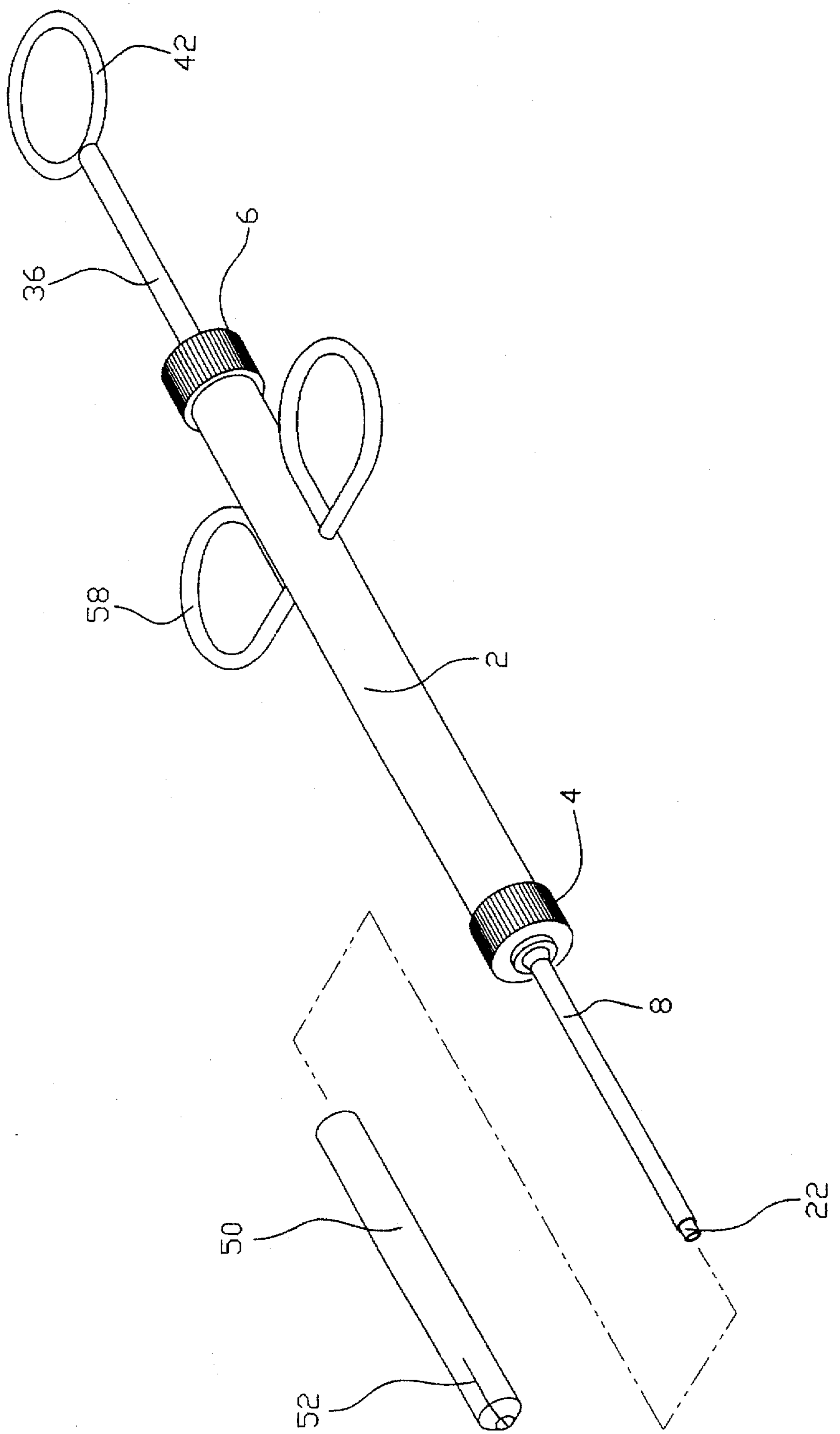
FIG. 1 is an isometric view of the pill dispensing syringe.
Figure 2:
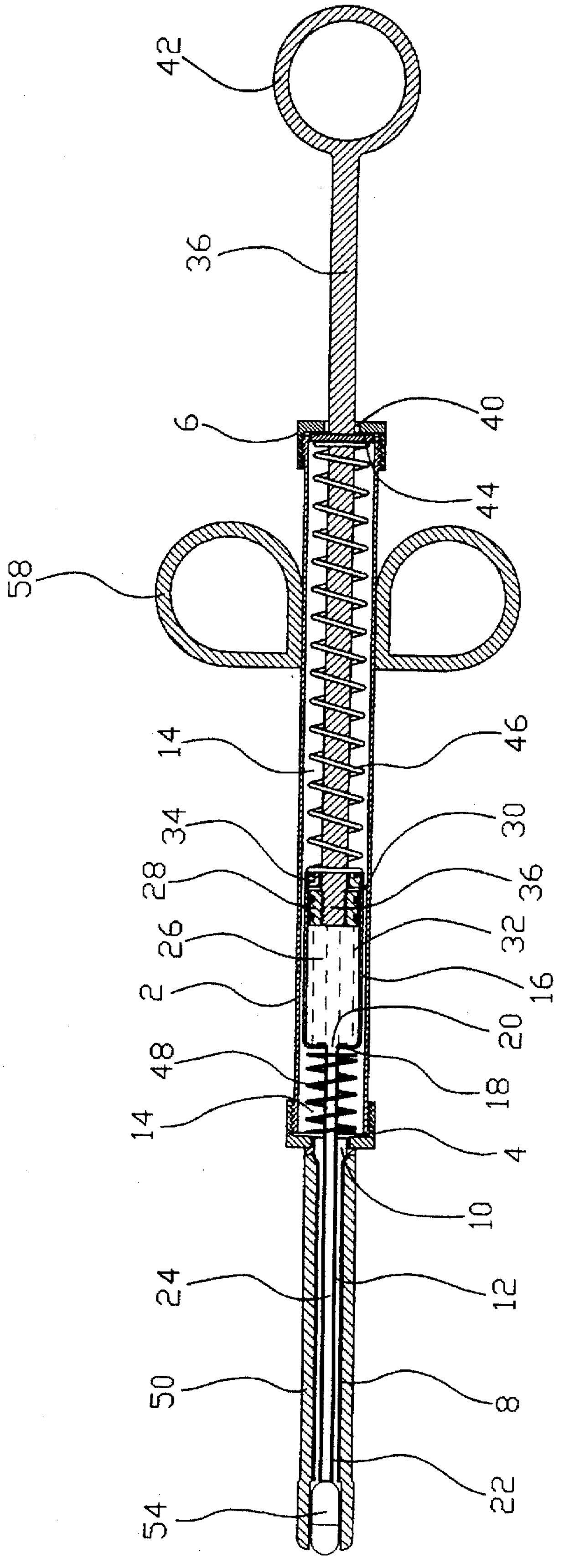
FIG. 2 is a midline cutaway view of the pill dispensing syringe.

Referring to FIG. 1, the pill dispensing syringe has a cylindrical outer housing 2 having a first end cap 4 covering its first end and a second end cap 6 covering its second end. Referring to FIG. 2, the end caps 4 and 6 are affixed to the first and second ends of the outer housing 2 by means of threaded fittings. Referring to FIG. 1, the end caps 4 and 6 have ridges on their outer radial surfaces allowing for manual tightening and removal of the end caps.

Figure 3:
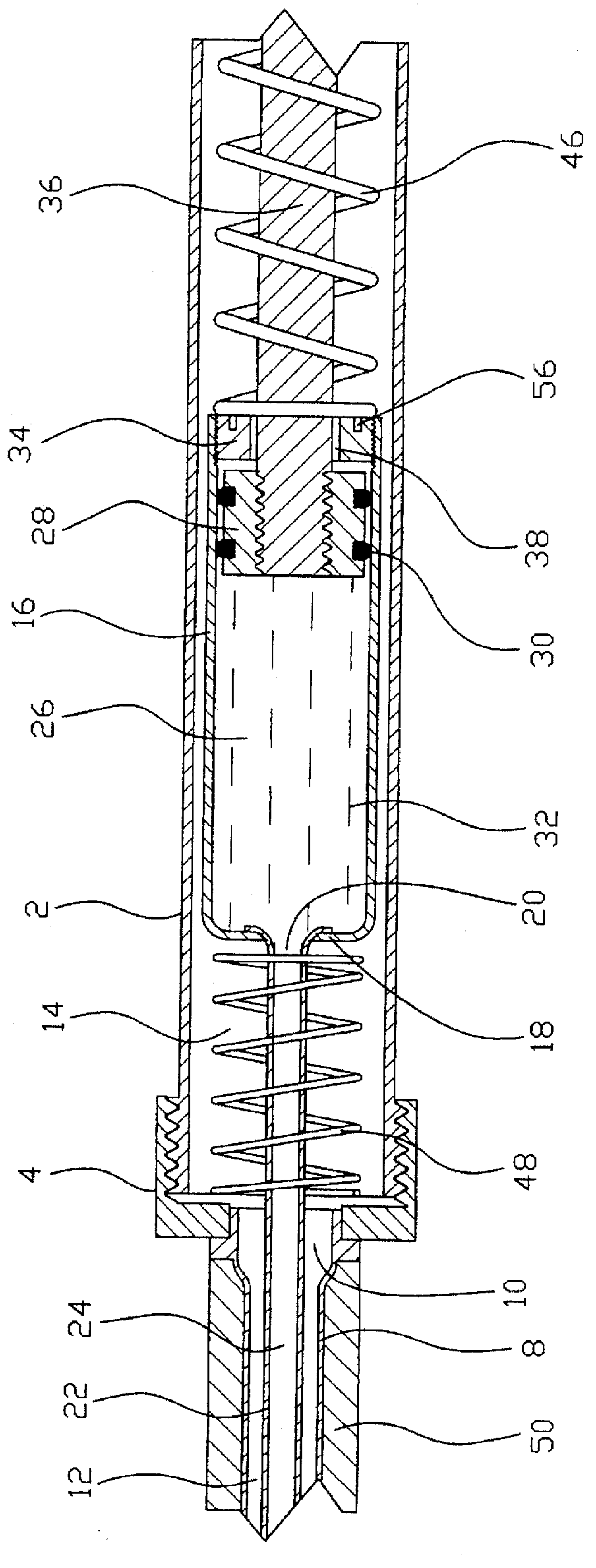
FIG. 3 is a magnified view of a portion of the cutaway view of FIG. 2.

A cylindrical outer sleeve 8 is fixedly attached to the first end of the first end cap 4. Referring to FIG. 3, the fixed attachment of outer sleeve 8 is accomplished by means of pressure fitting the outer sleeve 8 into a circular aperture 10 within the first end of the first end cap 4 so that the interior bore 12 of the outer sleeve 8 is continuous with the interior bore 14 of the outer housing 2.

Referring to FIG. 2, a water injection cylinder 16 is slidably mounted within the interior bore 14 of the outer housing 2. The water injection cylinder 16 has a floor 18, the floor 18 having a circular aperture 20. Referring to FIG. 1, a water injection tube 22 is slidably mounted within the outer sleeve 8. Referring to FIG. 2, the water injection tube 22 extends the length of the outer sleeve 8. Referring to FIG. 3, the water injection tube 22 further extends through the cylindrical aperture 10 of the first end cap 4 to protrude into the hollow interior bore 14 of the outer housing 2. The second end of the water injection tube 22 is fixedly attached to the edges of the aperture 20 within the floor 18 of the water injection cylinder 16 by means of a pressure fitting so that the interior bore 24 of the water injection tube 22 is continuous with the interior bore 26 of the water injection cylinder 16.

Referring further to FIG. 3, a piston 28 is slidably mounted within the interior bore 26 of the water injection cylinder 16, the piston 28 having a pair of rubber O-rings 30 mounted within a pair of annular channels within its outer radial surface. The O-rings 30 provide an occlusive seal between the inner radial surface of the water injection cylinder 16 and the outer radial surface of the piston 28. The O-rings 30 also provide increased friction between those two surfaces. The occlusive seal and the friction enables the piston to draw and drive water 32 into and out of the interior bore 26 of the water injection cylinder 16, and to impose thrust upon the water injection cylinder 16 and the water injection tube 22.

Referring further to FIG. 3, the second end of the water injection cylinder 16 has a circular piston retaining cap 34 mounted within the bore 26 of the water injection cylinder 16 by means of threads and fittings.

Referring further to FIG. 3, a piston rod 36 is fixedly attached to the piston 28 by means of threaded fittings, the piston rod 36 extending from the second end of the piston 28, and thence through a circular aperture 38 within the piston retaining cap 34.

Referring to FIG. 2, the piston rod 36 further extends along the interior bore of the outer housing 2 to extend through and protrude from a circular aperture 40 within the second end cap 6. Fixedly attached to the second end of the piston rod 36 is a thumb ring 42.

Referring further to FIG. 2, the piston rod 36 has an annular flange fixedly attached thereto at a point inside of the second end cap 6. A water drawing spring 46 is mounted over the piston rod 36 and within the interior bore 14 of the outer housing 2 so that it biases against and provides opposing force between the piston retaining cap 34 and the annular flange 44.

Referring further to FIG. 2, a thrust control spring 48 is mounted over the water injection tube 22 and within the interior bore 14 of the outer housing 2 so that it biases against and provides opposing force between the first end cap 4 and the floor 18 of the water injection cylinder 16. The thrust control spring 48 is selected so that its spring constant is less than that of the water drawing spring 46 allowing the water injection cylinder to be slidably driven toward the first end cap 4 by a thrust imposed by the piston rod 36 prior to commencement of motion of the piston 28 with respect to the water injection cylinder 16.

Referring to FIG. 1, a flexible and disposable pill retaining sleeve 50 is slidably mounted over the outer sleeve 8. The pill retaining sleeve 50 has a pill receiving slit 52 which is able to, referring to FIG. 2, flexibly expand and splay, allowing the pill retaining sleeve 50 to retain a pill 54. The interior bore of the pill retaining sleeve 50 is closely fitted to the exterior radial surface of the outer sleeve 8 so that the pill retaining sleeve 50 is firmly secured thereon while allowing manual installation and removal.

Referring to FIG. 3, the piston retaining cap 34 has a pair of apertures 56 facilitating installation and removal of the piston retaining cap 34 within the water injection cylinder by means of a two-pronged tool.

Referring to FIG. 1, a pair of finger loops 58 are fixedly attached to the exterior surface of the outer housing 2.

In operation, referring to FIG. 1, the pill dispensing syringe is grasped in the user's hand with the thumb placed through the thumb ring 42 and the index and middle fingers placed through the finger loops 58. With the pill dispensing syringe so held, the hand is closed causing the piston rod 36 to move toward the first end of the pill dispensing syringe.

Referring to FIG. 2, upon such movement of the piston rod 36, the thrust control spring 48 will begin to compress, allowing the water injection tube 22 to protrude from the first end of the outer sleeve 8. Upon further movement of the piston rod 36 toward its first end, the thrust control spring 48 becomes fully compressed. Upon further movement of the piston rod 36 toward its first end, the piston 28 is driven to the floor 18 of the water injection cylinder 16. The first end of the water injection tube 22 is then immersed in water, and the thumb of the user's hand is removed from the thumb ring 42. Upon release of the thumb ring 42, the water drawing spring 48 drives the piston rod 36 in the opposite direction, pulling the piston 28 toward the second end of the water injection cylinder 16. As the piston 28 moves from the floor 18 toward the piston retaining cap 34, water is drawn through the interior bore 24 of the water injection tube 22 through the aperture 20 within the floor 18 of the water injection cylinder 16; thus filling the interior space 26 of the water injection cylinder 16 with water 32.

Referring to FIG. 1, with the pill dispensing syringe filled with water, a pill retaining sleeve 50 is slidably mounted over the outer sleeve 8 and, referring simultaneously to FIGS. 1 and 2, a pill 54 is slidably positioned within the pill receiving slit 52. With the water injection cylinder filled and with the pill positioned as described above, the pill dispensing syringe is ready for use.

In use, referring to FIG. 2, the first end of the pill dispensing syringe is inserted into the mouth of an animal (such as a dog or cat) with the animal's head tilted slightly upwards. The pill dispensing syringe is grasped in the user's hand with the thumb through the thumb ring 42 and index and middle fingers through the finger loops 58. The user's hand is closed causing the thumb to drive the piston rod 36 and piston 28 in the direction of their first ends. Such thrusting of the piston rod 36 causes the water injection cylinder 16 and the water injection tube 22 to move toward their first ends. The first end of the water injection tube then contacts the pill 54, driving the pill out of the pill retaining slit 52 and into the animal's mouth. Upon further thrusting of the piston rod 36, the piston 28 is driven toward the floor 18 of the water injection cylinder 16 causing the water to emit through the interior bore 24 of the water injection tube 22 and into the animal's mouth. The presence of water in the animal's mouth invokes a swallowing response, causing the animal to swallow the pill. The pill dispensing syringe is then withdrawn.

Figure 4:
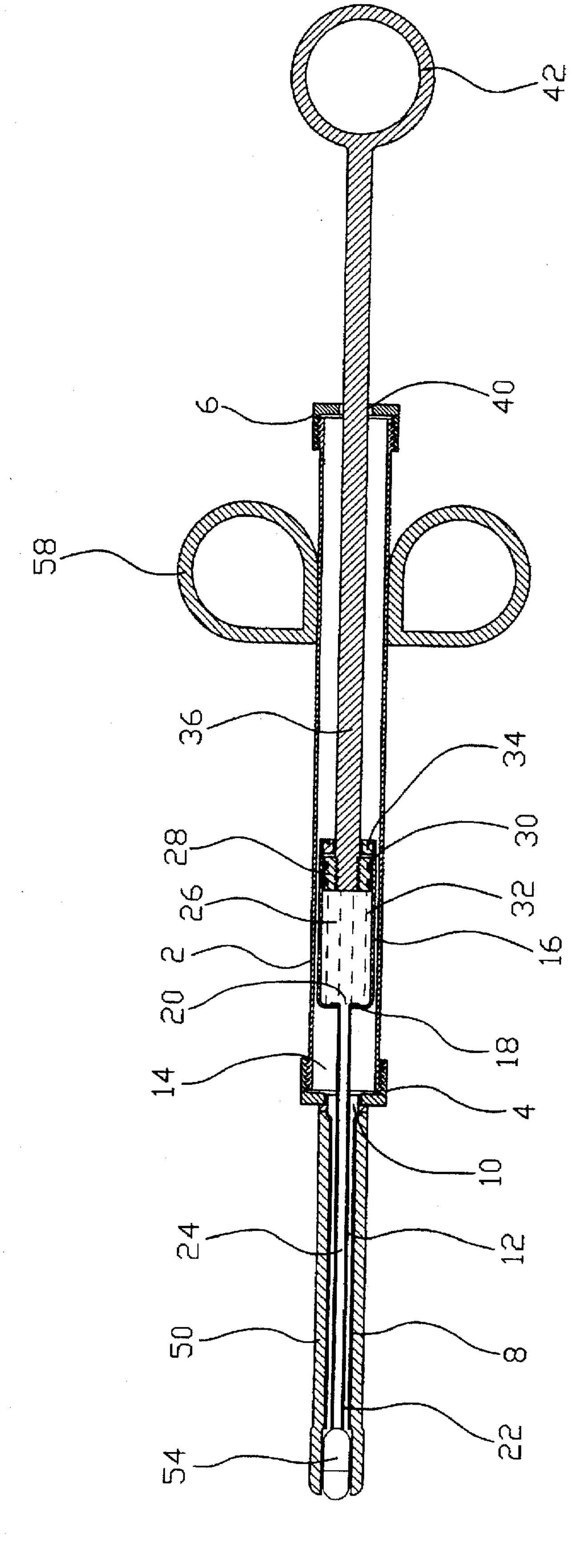
FIG. 4 is a cutaway view of an alternate configuration of the pill dispensing syringe.

FIG. 4 depicts an alternate construction of the pill dispensing syringe having all of the features disclosed in FIGS. 1, 2 and 3 but without, referring to FIG. 2, the thrust control spring 48, the water drawing spring 46, and without the annular flange 44. In use of this alternately constructed pill dispensing syringe, water is drawn into the water injection cylinder 16 by holding the extended end of the water injection tube 22 between the fingers of a hand of the user, immersing the end of the water injection tube 22 in water, and causing the thumb of the user's other hand to draw the thumb ring 42 upward, causing water to fill the water injection cylinder 16. Friction between the O-rings 30 and the internal wall of the water injection cylinder 16 allows thrust imposed upon the piston rod 36 to drive the pill 54 into the animal's mouth prior to the injection of water into the animal's mouth.

All of the elements and features described above, except for the pill retaining sleeve 50 and the O-rings 30, preferably are composed of stainless steel. The O-rings 30 preferably are composed of highly durable vulcanized rubber, and the pill retaining sleeve 50 preferably is composed of latex rubber which may be economically disposed of and replaced allowing sterile use of the pill dispensing syringe with several animals in sequence.

The threaded fittings of the end caps 4 and 6, of the piston 28 and of the piston retaining cap 34 allow the pill dispensing syringe to be easily assembled and disassembled for sterilization purposes.

There are various changes and modifications which may be made to the invention as would be apparent to those skilled in the art. However, these changes or modifications are included in the teaching of the disclosure and it is intended that the invention be limited only by the scope of the claims appended hereto.

We claim:

1. A pill dispensing syringe comprising:

(A) A cylindrical outer housing, the outer housing having a first end and a second end, (B) A water injection cylinder slidably mounted within the interior bore of the outer housing, the water injection cylinder having a first end and a second end, (C) A piston slidably mounted within the interior bore of the water injection cylinder, the piston having a first end and a second end;

(D) A piston rod having a first end and a second end, the first end of the piston rod being fixedly attached to the second end of the piston, and the piston rod extending from the second end of the piston along the interior bores of the water injection cylinder and the outer housing to protrude from their second ends, (E) A cylindrical pill dispensing sleeve, the pill dispensing sleeve having a first end and a second end, the first end of the pill dispensing sleeve being adapted for holding a pill, and the second end of the pill dispensing sleeve being fixedly attached to the first end of the outer housing so that the interior bore of the pill dispensing sleeve is continuous with the interior bore of the outer housing, and, (F) A cylindrical water injection tube, the water injection tube having a first end and a second end, the water injection tube being slidably mounted within the interior bore of the pill dispensing sleeve so that the second end of the water injection tube protrudes from the second end of the pill dispensing sleeve, the second end of the water injection tube being fixedly attached to the first end of the water injection cylinder so that the interior bore of the water injection tube is continuous with the interior bore of the water injection cylinder, and the longitudinal dimension of the water injection tube being sized and fitted so that upon sliding motion of the water injection cylinder and the water injection tube in the direction of their first ends within the interior bores of the pill dispensing sleeve and the outer housing, the first end of the water injection tube may come into contact with a pill held by the first end of the pill dispensing sleeve.

2. The apparatus of claim No. 1 wherein the pill dispensing sleeve comprises an inner sleeve forming the interior bore of the pill dispensing sleeve and a flexible outer sleeve, the inner sleeve and flexible outer sleeve each having a first end and a second end, the interior bore of the flexible outer sleeve being closely fitted to and slidably mounted over the outer surface of the inner sleeve so that the first end of the flexible outer sleeve extends from the first end of the inner sleeve and so that the second end of the inner sleeve extends from the second end of the flexible outer sleeve, the fixed attachment of the pill dispensing sleeve to the outer housing being at the second end of the inner sleeve, and the adaptation for holding a pill being at the first end of the flexible outer sleeve.

3. The apparatus of claim No. 1 wherein the piston rod has fixedly attached thereto an annular flange having a first end and a second end, and further comprising a water drawing spring, the water drawing spring having a first end and a second end, the water drawing spring being mounted over the piston rod so that the first end of the water drawing spring may come into contact with the second end of the water injection cylinder, and so that the second end of the water drawing spring may come into contact with the first end of the annular flange.

4. The apparatus of claim No. 2 wherein the piston rod has fixedly attached thereto an annular flange having a first end and a second end, and further comprising a water drawing spring, the water drawing spring having a first end and a second end, the water drawing spring being mounted over the piston rod so that the first end of the water drawing spring may come into contact with the second end of the water injection cylinder, and so that the second end of the water drawing spring may come into contact with the first end of the annular flange.

5. The apparatus of claim No. 1 further comprising a thrust control spring having a first end and a second end, the thrust control spring being mounted over the water injection tube so that the first end of the thrust control spring may come into contact with the second end of the pill dispensing sleeve, and so that the second end of the thrust control spring may come into contact with the first end of the water injection cylinder.

6. The apparatus of claim No. 2 further comprising a thrust control spring having a first end and a second end, the thrust control spring being mounted over the water injection tube so that the first end of the thrust control spring may come into contact with the second end of the pill dispensing sleeve, and so that the second end of the thrust control spring may come into contact with the first end of the water injection cylinder.

7. The apparatus of claim No. 3 further comprising a thrust control spring having a first end and a second end, the thrust control spring being mounted over the water injection tube so that the first end of the thrust control spring may come into contact with the second end of the pill dispensing sleeve, and so that the second end of the thrust control spring may come into contact with the first end of the water injection cylinder.

8. The apparatus of claim No. 4 further comprising a thrust control spring having a first end and a second end, the thrust control spring being mounted over the water injection tube so that the first end of the thrust control spring may come into contact with the second end of the pill dispensing sleeve, and so that the second end of the thrust control spring may come into contact with the first end of the water injection cylinder.

9. The apparatus of claim No. 7 wherein the piston has a plurality of annular channels within its outer radial surface and further comprising a plurality of flexible O-rings, the O-rings being closely fitted to and mounted within the annular channels, the O-rings providing an occlusive seal between and increased friction between the interior surface of the water injection cylinder and the exterior surface of the piston.

10. The apparatus of claim No. 8 wherein the piston has a plurality of annular channels within its outer radial surface and further comprising a plurality of flexible O-rings, the O-rings being closely fitted to and mounted within the annular channels, the O-rings providing an occlusive seal between and increased friction between the interior surface of the water injection cylinder and the exterior surface of the piston.

11. The apparatus of claim No. 9 further comprising a pair of finger loops fixedly attached to the exterior wall of the outer housing and extending radially outward therefrom.

12. The apparatus of claim No. 10 further comprising a pair of finger loops fixedly attached to the exterior wall of the outer housing, and extending radially outward therefrom.

13. The apparatus of claim No. 11 further comprising a thumb ring fixedly attached to the second end of the piston rod.

14. The apparatus of claim No. 12 further comprising a thumb ring fixedly attached to the second end of the piston rod.

* * * * *